United States Patent
Tybinkowski et al.

(10) Patent No.: US 7,438,471 B2
(45) Date of Patent: *Oct. 21, 2008

(54) MOBILE COMPUTERIZED TOMOGRAPHY (CT) IMAGING SYSTEM WITH FRAME/BEARING/DRUM CONSTRUCTION

(75) Inventors: Andrew P. Tybinkowski, Boxford, MA (US); Eric M. Bailey, Hampton, NH (US); James P. Flinn, Boston, MA (US); Michael J. Duffy, Methuen, MA (US)

(73) Assignee: NeuroLogica Corp., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/653,705

(22) Filed: Jan. 16, 2007

(65) Prior Publication Data

US 2007/0183589 A1   Aug. 9, 2007

Related U.S. Application Data

(63) Continuation-in-part of application No. 11/193,941, filed on Jul. 29, 2005, now Pat. No. 7,175,347.

(60) Provisional application No. 60/670,164, filed on Apr. 11, 2005, provisional application No. 60/593,001, filed on Jul. 30, 2004.

(51) Int. Cl.
*H05G 1/02* (2006.01)
*H05G 1/60* (2006.01)

(52) U.S. Cl. ............................. 378/198; 378/197; 378/4

(58) Field of Classification Search ................ 378/4, 378/15, 19, 20, 193–198, 405–208, 205; 250/370.09
See application file for complete search history.

(56) References Cited

U.S. PATENT DOCUMENTS

| | | | |
|---|---|---|---|
| 3,603,975 A | | 9/1971 | Gordon |
| 5,638,419 A | * | 6/1997 | Ingwersen .................... 378/4 |
| 5,887,047 A | | 3/1999 | Bailey et al. |
| 5,937,028 A | | 8/1999 | Tybinkowski et al. |
| 5,982,843 A | | 11/1999 | Bailey et al. |
| 5,982,844 A | | 11/1999 | Tybinkowski et al. |
| 6,108,396 A | | 8/2000 | Bechwati et al. |
| 6,188,743 B1 | | 2/2001 | Tybinkowski et al. |
| 6,256,404 B1 | | 7/2001 | Gordon et al. |
| 6,285,028 B1 | | 9/2001 | Yamakawa |
| 6,337,894 B1 | | 1/2002 | Tybinkowski et al. |
| 6,396,902 B2 | | 5/2002 | Tybinkowski et al. |
| 6,449,340 B1 | | 9/2002 | Tybinkowski et al. |
| 6,452,998 B2 | | 9/2002 | Tybinkowski et al. |

(Continued)

*Primary Examiner*—Irakli Kiknadze
(74) *Attorney, Agent, or Firm*—Pandiscio & Pandiscio

(57) ABSTRACT

A CT imaging system comprising a frame having a center opening and a uni-body construction; a CT imaging unit mounted to the frame and comprising: a rotatable drum assembly rotatably mounted to the frame, concentric with the center opening, wherein at least one bearing is disposed between the rotatable drum assembly and the frame, and further wherein one race of the bearing is formed by a surface of the rotatable drum assembly and the other race of the bearing is formed by a surface of the frame; an X-ray tube mounted on the rotatable drum assembly; and an X-ray detector mounted on the rotatable drum assembly in alignment with the X-ray beam; and a transport mechanism mounted to the frame, the transport mechanism comprising a fine movement mechanism for moving the CT imaging unit precisely, relative to the patient, during scanning.

11 Claims, 9 Drawing Sheets

U.S. PATENT DOCUMENTS

| | | |
|---|---|---|
| 6,519,312 B1 | 2/2003 | Tybinkowski et al. |
| 6,556,657 B1 | 4/2003 | Tybinkowski et al. |
| 6,721,388 B2 | 4/2004 | Tybinkowski et al. |
| 6,813,374 B1 | 11/2004 | Karimi et al. |
| 6,857,778 B2 | 2/2005 | Mun et al. |
| 7,175,347 B2 * | 2/2007 | Tybinkowski et al. ....... 378/198 |
| 2007/0183588 A1 | 8/2007 | Bailey et al. |
| 2007/0183589 A1 | 8/2007 | Tybinkowski et al. |
| 2007/0195938 A1 | 8/2007 | Bailey et al. |

\* cited by examiner

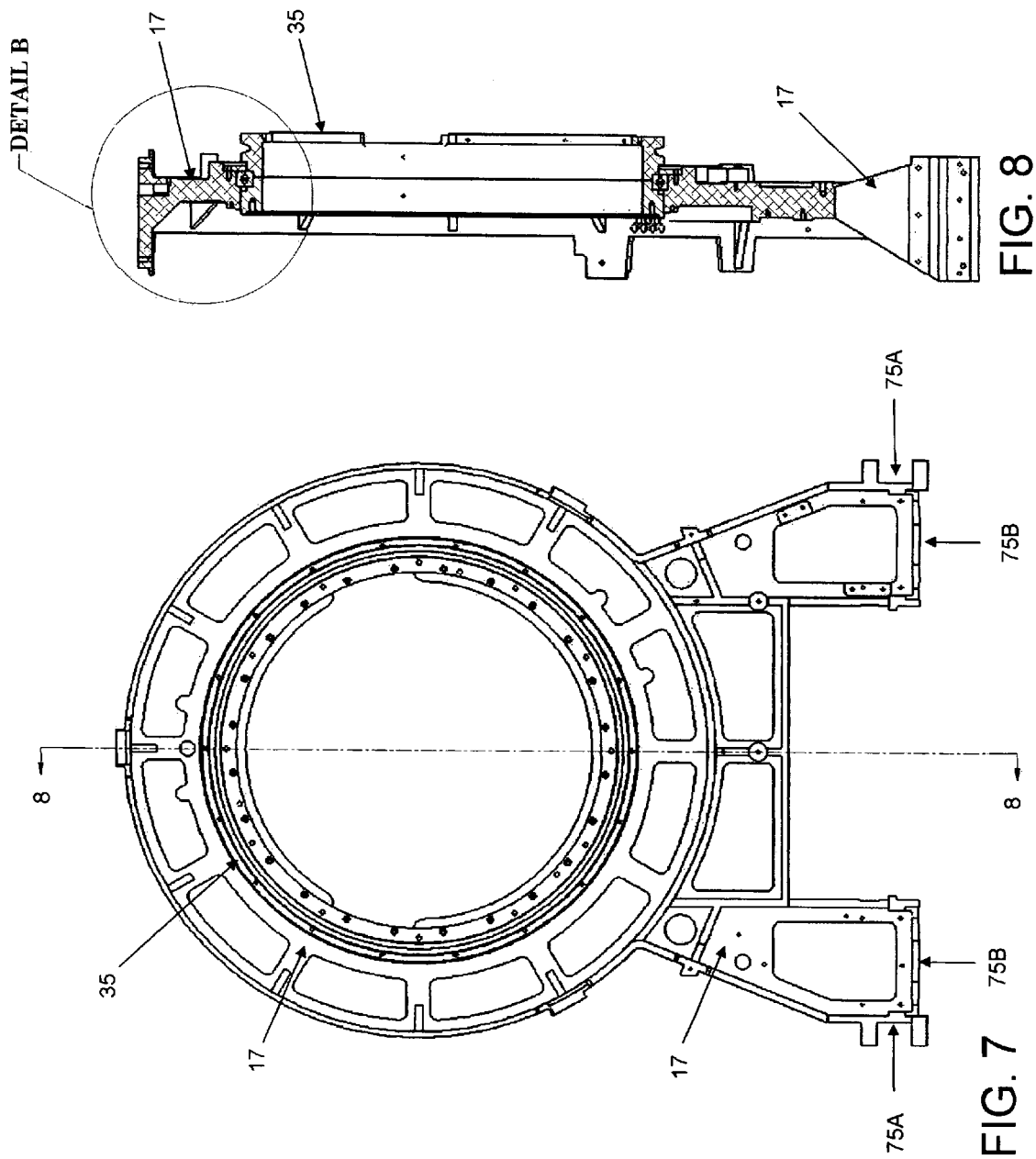

MOBILE COMPUTERIZED TOMOGRAPHY (CT) IMAGING SYSTEM WITH FRAME/BEARING/DRUM CONSTRUCTION

REFERENCE TO PENDING PRIOR APPLICATIONS

This patent application is a continuation-in-part of prior U.S. patent application Ser. No. 11/193,941, filed Jul. 29, 2005 now U.S. Pat. No. 7,175,347 by Andrew P. Tybinkowski et al. for ANATOMICAL IMAGING SYSTEM WITH CENTIPEDE DRIVE, which patent application in turn claims benefit of:

(i) prior U.S. Provisional Patent Application Ser. No. 60/670,164, filed Apr. 11, 2005 by Andrew P. Tybinkowski et al. for ANATOMICAL IMAGING SYSTEM WITH CENTIPEDE DRIVE; and (ii) prior U.S. Provisional Patent Application Ser. No. 60/593,001, filed Jul. 30, 2004 by Bernard Gordon et al. for ANATOMICAL SCANNING SYSTEM.

The three above-identified patent applications are hereby incorporated herein by reference.

FIELD OF THE INVENTION

This invention relates to anatomical imaging systems in general, and more particularly to Computerized Tomography (CT) imaging systems.

BACKGROUND OF THE INVENTION

Strokes are currently the third leading cause of death in the United States, causing approximately 177,000 deaths per year, and strokes are currently the number one cause of long-term disability in the United States, affecting nearly 5 million people. Strokes are caused by an abrupt interruption of the blood supply to the brain or spinal cord, thereby depriving the tissue of oxygen and resulting in tissue damage.

Strokes typically occur in one of two forms: (i) hemorrhagic stokes, which occur with the rupture of a blood vessel; and (ii) ischemic strokes, which occur with the obstruction of a blood vessel.

Rapid diagnosis is a key component of stroke treatment. This is because the treatment for an ischemic stroke may be contra-indicated for the treatment for a hemorrhagic stroke and, furthermore, the effectiveness of a particular treatment may be time-sensitive. More particularly, the current preferred treatment for an acute ischemic stroke, i.e., the administration of tPA to eliminate blood clots, is contra-indicated for a hemorrhagic stroke. Furthermore, the clinical data suggests that the medication used to treat ischemic strokes (i.e., tPA.) is most effective if it is administered within 3 hours of the onset of the stroke. However, current diagnosis times, i.e., the time needed to identify that the patient is suffering from a stroke and to identify the hemorrhagic or ischemic nature of the stroke, frequently exceeds this 3 hour window. As a result, only a fraction of current ischemic stroke victims are timely treated with tPA.

Imaging is generally necessary to properly diagnose (and hence properly treat) a stroke. More particularly, imaging is generally necessary to: (i) distinguish strokes from other medical conditions; (ii) distinguish between the different types of strokes (i.e., hemorrhagic or ischemic); and (iii) determine appropriate treatments (e.g., the administration of tPA in the case of an ischemic stroke).

Computerized Tomography (CT) has emerged as the key imaging modality in the diagnosis of strokes. CT imaging systems generally operate by directing X-rays into the body from a variety of positions, detecting the X-rays passing through the body, and then processing the detected X-rays so as to build a computer model of the patient's anatomy. This computer model can then be visualized so as to provide images of the patient's anatomy. It has been found that such CT scanning, including non-enhanced CT scanning, CT angiography scanning and CT perfusion scanning, is able to provide substantially all of the information needed to effectively diagnose (and hence properly treat) a stroke.

Unfortunately, in practice, the CT imaging system is typically located in the hospital's radiology department and the patient is typically received in the hospital's emergency room, and the "round-trip" time between the emergency room and the radiology department can frequently involve substantial delays, even in the best of hospitals. As a result, the time spent in transporting the patient from the emergency room to the radiology department and then back again can consume critical time which can compromise proper treatment of the patient (e.g., it can prevent ischemic stroke victims from being timely treated with tPA).

Thus, there is an urgent need for a new and improved CT imaging system which is particularly well suited for use in stroke applications. More particularly, there is an urgent need for a small, mobile CT imaging system which can be pre-positioned in the emergency room and moved to the patient so that the patient can be scanned at their current location, thus effectively eliminating "round-trip" delays and dramatically reducing the time needed to properly diagnose the patient. It is also important that the CT imaging system be relatively inexpensive, so as to facilitate its rapid proliferation and widespread use, e.g., pre-positioning in substantially all hospital emergency rooms and wide availability in outlying, low-volume settings (e.g., rural hospitals, ships, etc.).

In this respect it should also be appreciated that current CT imaging systems are generally quite complex, in both a mechanical sense and in an electrical sense. This is due to the general nature of CT imaging systems.

More particularly, current CT imaging systems generally comprise a frame which supports a rotating drum assembly having a center opening, an X-ray tube assembly adapted to emit X-rays, and an X-ray detector assembly adapted to detect X-rays. The X-ray tube assembly and the X-ray detector assembly are mounted to the rotating drum assembly about the center opening, in diametrically-opposing relation, such that the X-ray beam (generated by the X-ray tube assembly and detected by the X-ray detector assembly) is passed through the interior of the drum assembly (i.e., across the center opening), and hence is passed through patient anatomy disposed within the interior of the rotating drum assembly (i.e., patient anatomy disposed within the center opening). Furthermore, since the X-ray tube assembly and the X-ray detector assembly are mounted on the rotating drum assembly so that they are rotated concentrically about the axis of the rotating drum assembly, the X-ray beam will be passed through the patient's anatomy along a full range of radial positions. As a result, by moving the patient longitudinally through the center opening while passing the X-ray beam through the anatomy along a range of radial positions, the CT imaging system can create the desired computer model of the scanned anatomy. Thus it will be appreciated that CT imaging systems must provide the mechanical systems needed for mounting the rotating drum assembly to the frame in a manner that frictionlessly supports the substantial weight of the rotating drum assembly and its passenger components (e.g., the X-ray tube assembly and the X-ray detector assembly).

Due to their nature, the frame, the rotating drum assembly and the mechanical mounts tend to be relatively complex and costly to produce.

Thus, there is a need for a new and improved approach for forming the frame, the rotating drum assembly and the mechanical mounts, and for mounting the rotating drum assembly and its passenger components (e.g., the X-ray tube assembly and the X-ray detector assembly) to the frame, so as to facilitate the provision of a mobile CT imaging system of reduced complexity and reduced cost.

SUMMARY OF THE INVENTION

In accordance with the present invention, there is provided a novel approach for forming the frame, the rotating drum assembly and the mechanical mounts, and for mounting the rotating drum assembly and its passenger components (e.g., the X-ray tube assembly and the X-ray detector assembly) to the frame, so as to facilitate the provision of a mobile CT imaging system of reduced complexity and reduced cost.

In one form of the invention, there is provided a mobile CT imaging system comprising:

a frame having a center opening, the frame being formed with a uni-body construction;

a CT imaging unit mounted to the frame, wherein the CT imaging unit is adapted to scan anatomical objects located within the center opening and generate images of the same, wherein the CT imaging unit comprises:

a rotatable drum assembly rotatably mounted to the frame, concentric with the center opening, wherein at least one bearing is disposed between the rotatable drum assembly and the frame, and further wherein one race of the bearing is formed by a surface of the rotatable drum assembly and the other race of the bearing is formed by a surface of the frame;

an X-ray tube mounted on the rotatable drum assembly and configured to emit an X-ray beam; and an X-ray detector mounted on the rotatable drum assembly in alignment with the X-ray beam; and a transport mechanism mounted to the frame, wherein the transport mechanism comprises a fine movement mechanism for moving the CT imaging unit precisely, relative to the patient, during scanning.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 7 is a schematic front view of another frame and another rotating drum assembly of the novel mobile CT imaging system shown in FIGS. 1-3;

FIG. 8 is a schematic sectional view taken along lines 8-8 of FIG. 7;

DETAILED DESCRIPTION OF THE PREFERRED EMBODIMENTS

Figure 1:
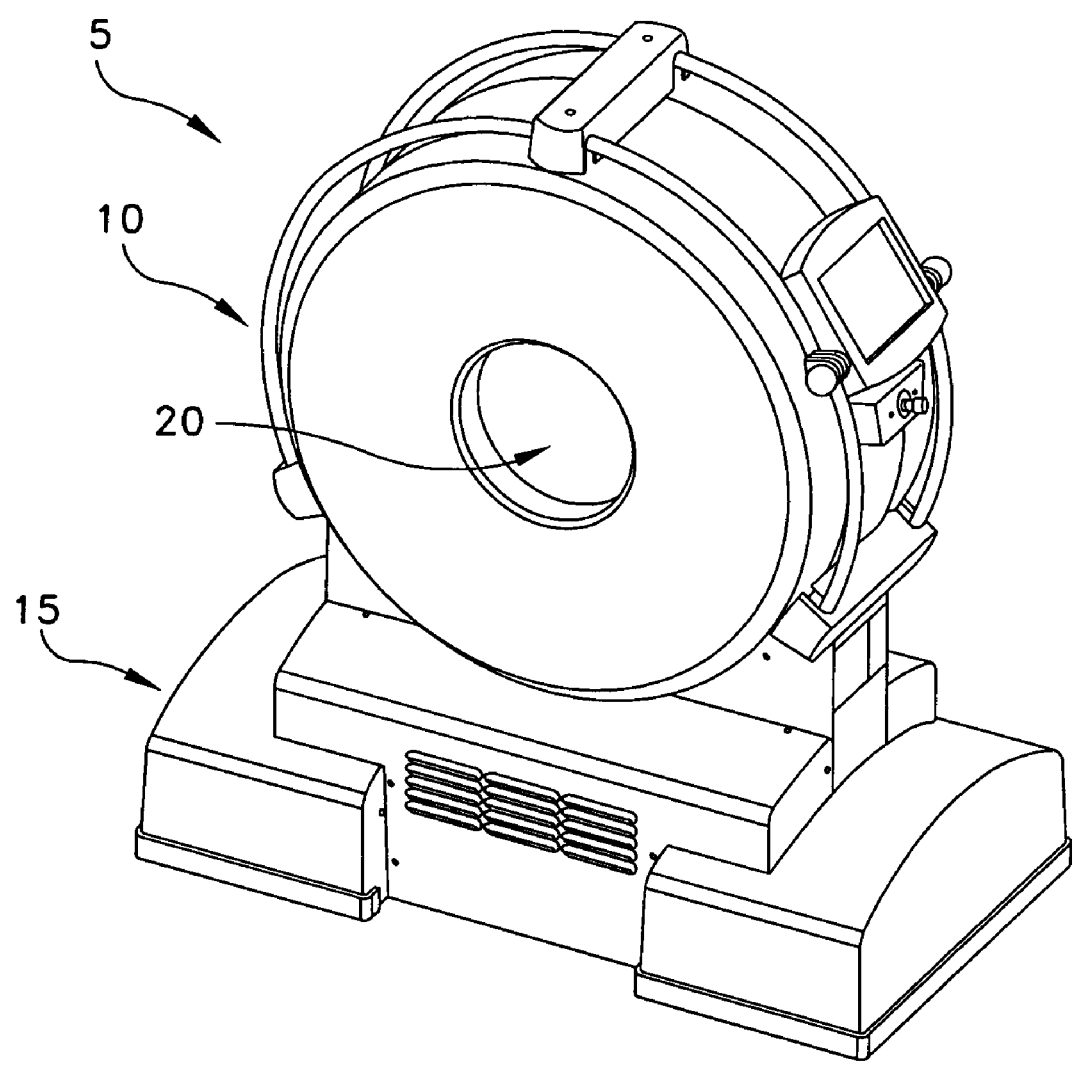
FIGS. 1 and 2 are schematic external views of a novel mobile-CT imaging system formed in accordance with the present invention.
Figure 2:
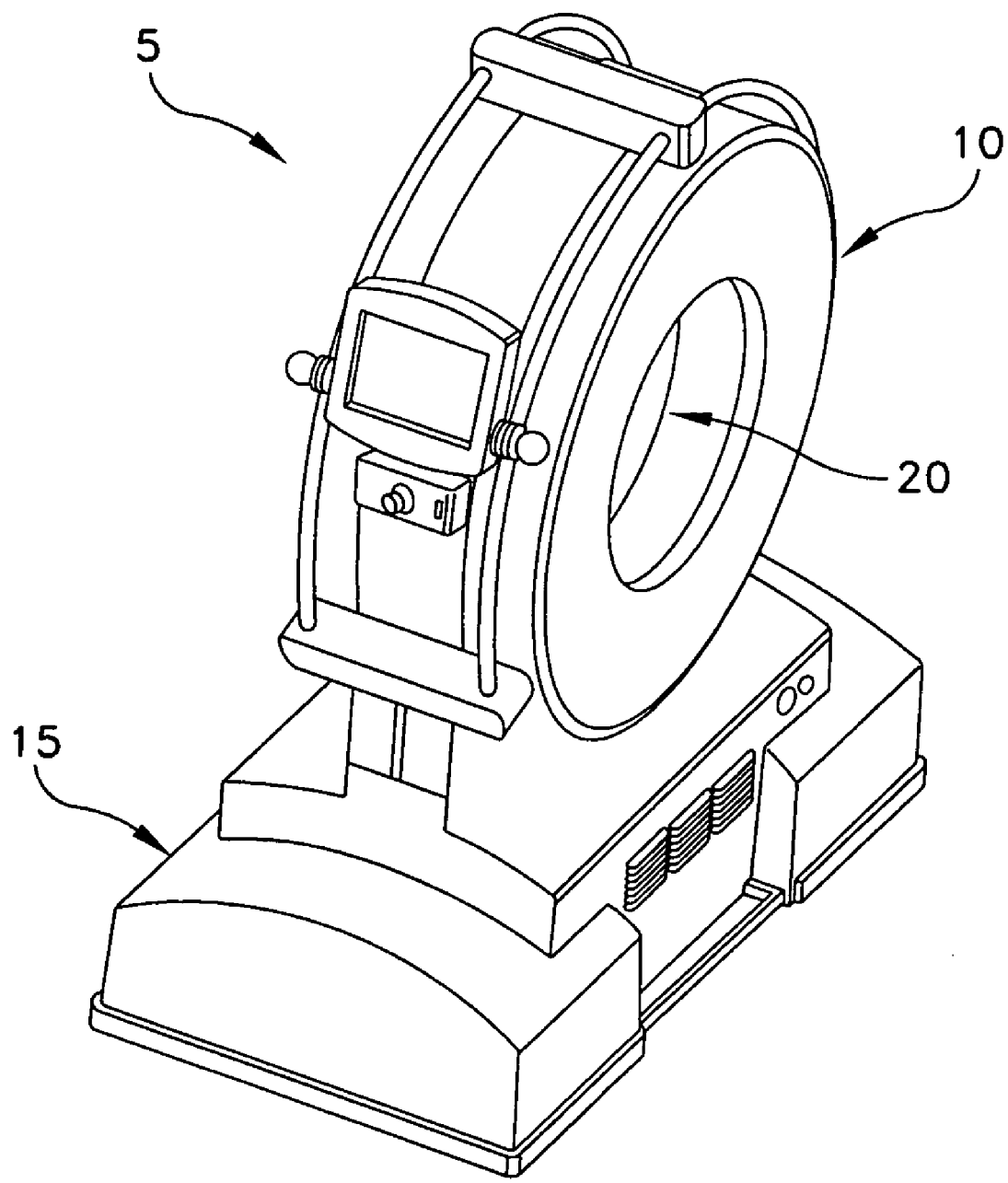
Figure 3:
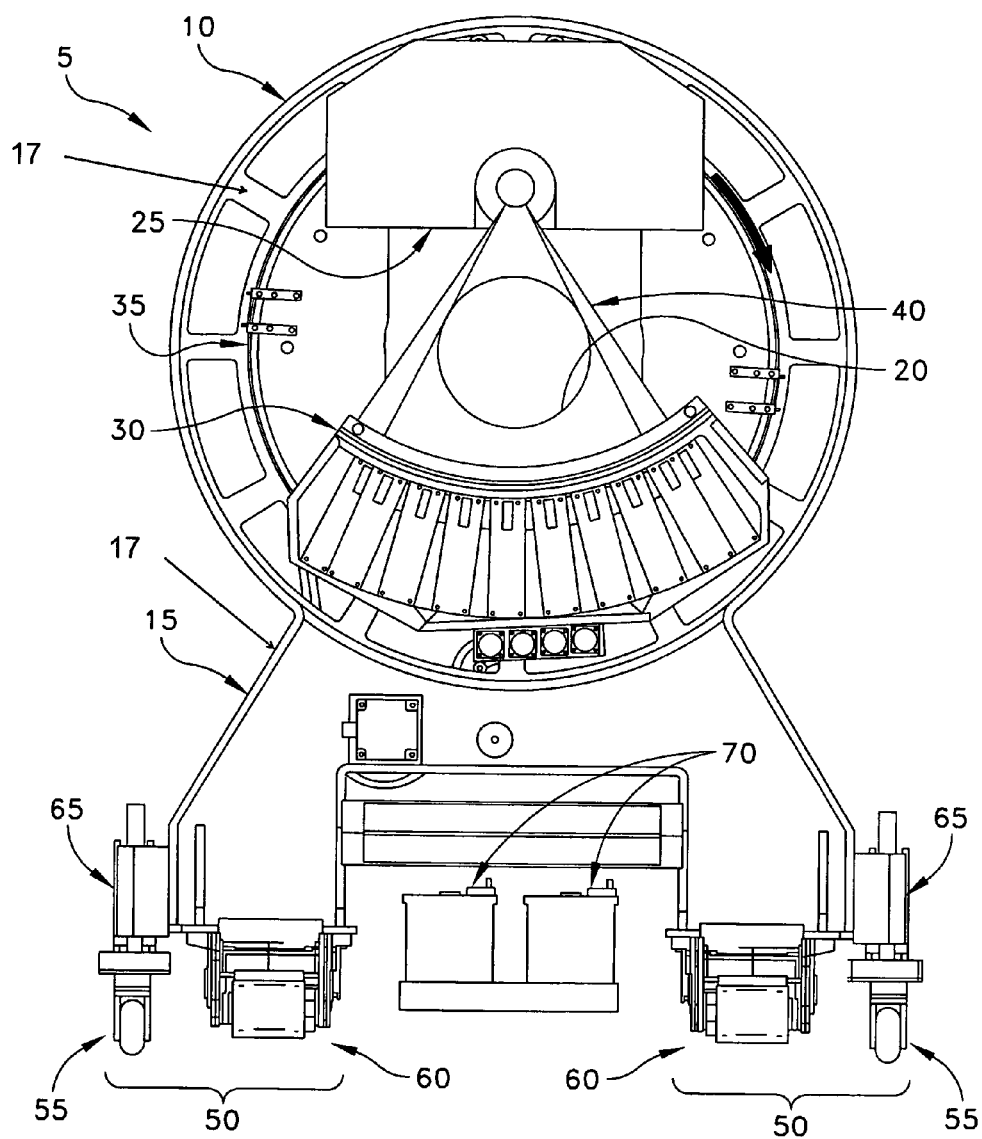
FIG. 3 is a schematic internal view of the novel mobile CT imaging system shown in FIGS. 1 and 2.

Looking now at FIGS. 1-3, there is shown a novel mobile CT imaging system 5 formed in accordance with the present invention. Mobile CT imaging system 5 generally comprises a torus 10 which is supported by a base 15. More particularly, mobile CT imaging system 5 comprises a frame 17 (FIG. 3) which forms and/or supports torus 10 and base 15. A center opening 20 is formed in torus 10. Center opening 20 receives the patient anatomy which is to be scanned, i.e., the head of the patient when mobile CT imaging system 5 is to be used in stroke applications.

As seen in FIG. 3, torus 10 generally comprises a X-ray tube assembly 25, an X-ray detector assembly 30, and a rotating drum assembly 35. X-ray tube assembly 25 and X-ray detector assembly 30 are mounted to rotating drum assembly 35 in diametrically-opposing relation, such that the X-ray beam 40 (generated by X-ray tube assembly 25 and detected by X-ray detector assembly 30) is passed through patient anatomy disposed in center opening 20. Furthermore, since X-ray tube assembly 25 and X-ray detector assembly 30 are mounted on rotating drum assembly 35 so that they are rotated concentrically about center opening 20, X-ray beam 40 will be passed through the patient's anatomy along a full range of radial positions. As a result, by passing the X-ray beam through the anatomy along a range of radial positions, while also passing the X-ray beam through the anatomy along a range of longitudinal positions, mobile CT imaging system 5 can create the desired computer model of the scanned anatomy. Significantly, with mobile CT imaging system 5, scanning is conducted while the patient remains stationary and the CT imaging system is moved, as will hereinafter be discussed in further detail.

The various electronic hardware and software for controlling the operation of X-ray tube assembly 25, X-ray detector assembly 30, and rotating drum assembly 35, as well as for processing the acquired scan data so as to generate the desired computer model and images, may be of the sort well known in the art and may be located in torus 10 and/or base 15.

Still looking now at FIG. 3, base 15 comprises a transport assembly 50 for moving mobile CT imaging system 5 about relative to the patient. More particularly, as disclosed in the aforementioned U.S. patent application Ser. No. 11/193,941, which patent application is hereby incorporated herein by reference, transport assembly 50 preferably comprises (i) a gross movement mechanism 55 for moving mobile CT imaging system 5 relatively quickly across room distances, so that the mobile CT imaging system can be quickly and easily brought to the patient, and (ii) a fine movement mechanism 60 for moving the mobile CT imaging system precisely, relative to the patient, during scanning, so that the patient can be scanned without being moved. As discussed in detail in the aforementioned U.S. patent application Ser. No. 11/193,941, gross movement mechanism 55 preferably comprises a plurality of free-rolling casters, and fine movement mechanism 60 preferably comprises a plurality of centipede belt drives (which can be configured for either stepped or continuous motion, whereby to provide either stepped or continuous scanning). Hydraulic apparatus 65 permits either gross movement mechanism 55 or fine movement mechanism 60 to be engaged with the floor, whereby to facilitate appropriate movement of the mobile CT imaging system 5. However, as also discussed in detail in the aforementioned U.S. patent application Ser. No. 11/193,941, gross movement mechanism 55 may be omitted entirely, and only fine movement mechanism 60 may be provided, in which case fine movement mechanism 60 is used to both (i) move mobile CT imaging system 5 to the patient prior to scanning, and (ii) move the mobile CT imaging system relative to the patient during scanning.

Base 15 preferably also includes other system components in addition to those discussed above, e.g., batteries 70 for powering the electrical components of CT machine 5, etc.

The various components of CT imaging system 5 are engineered so as to reduce the complexity and cost of frame 17, rotating drum assembly 35, and the mechanical mounts (e.g., bearings) disposed therebetween. Among other things, and as will hereinafter be discussed in further detail, frame 17 of mobile CT imaging system 5 comprises a singular (e.g., unibody or one-piece) construction, connecting (at its bottom end) directly to transport mechanism 50, and serving (at its top end) as one race for a bearing mechanism interposed between frame 17 and rotating drum assembly 35, as will hereinafter be discussed in further detail. This novel construction permits the CT imaging system to be less complex to manufacture and less costly to produce.

Frame/Bearing/Drum Construction

Figure 5:
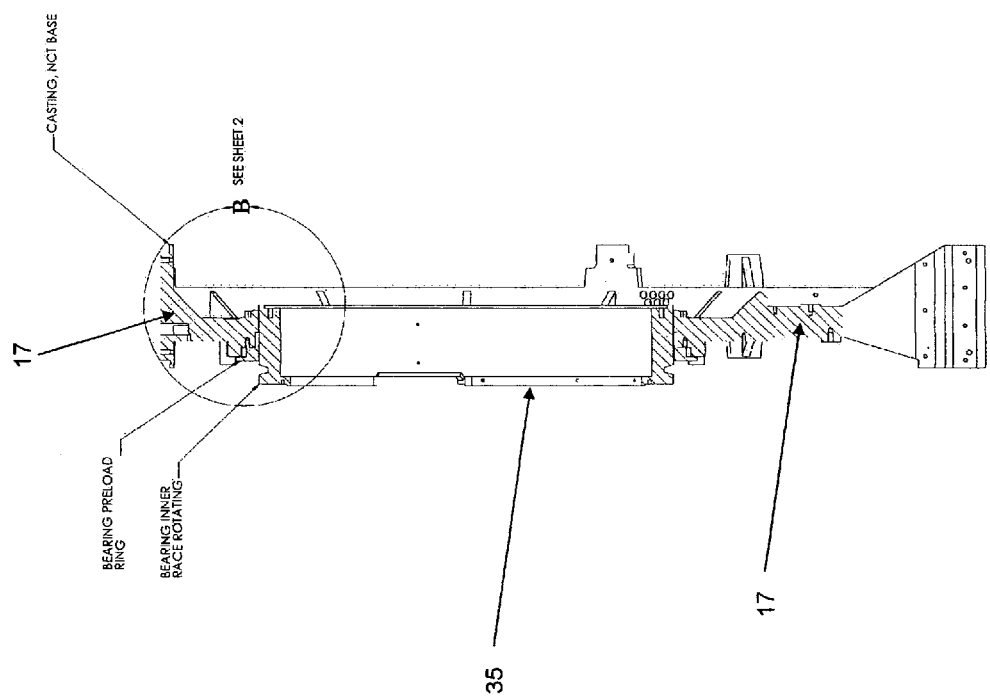
FIG. 5 is a schematic sectional view taken along lines 5-5 of FIG. 4.
Figure 6:
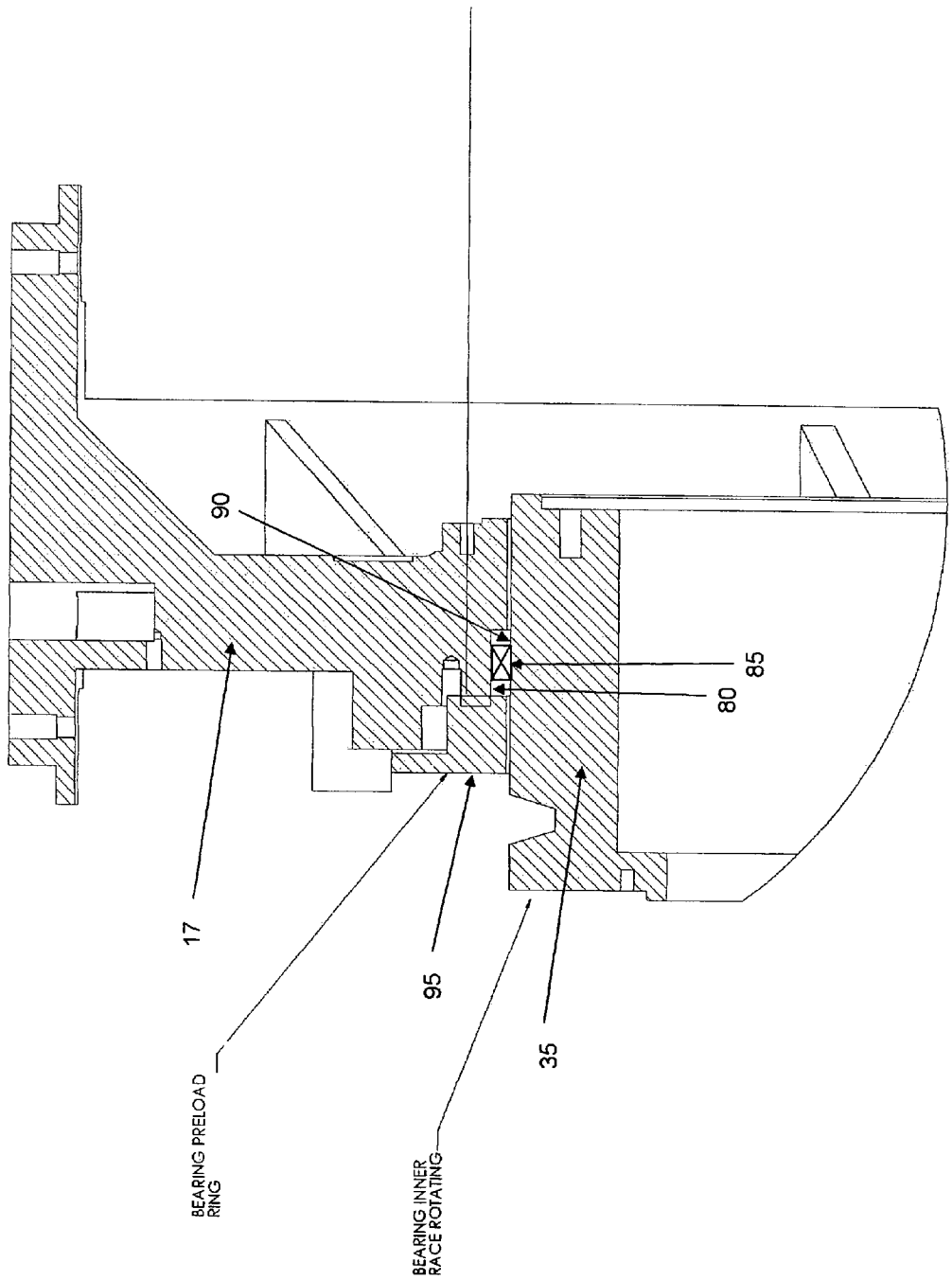
FIG. 6 is a schematic enlarged view of portions of the frame and rotating drum assembly shown in FIG. 5.
Figure 9:
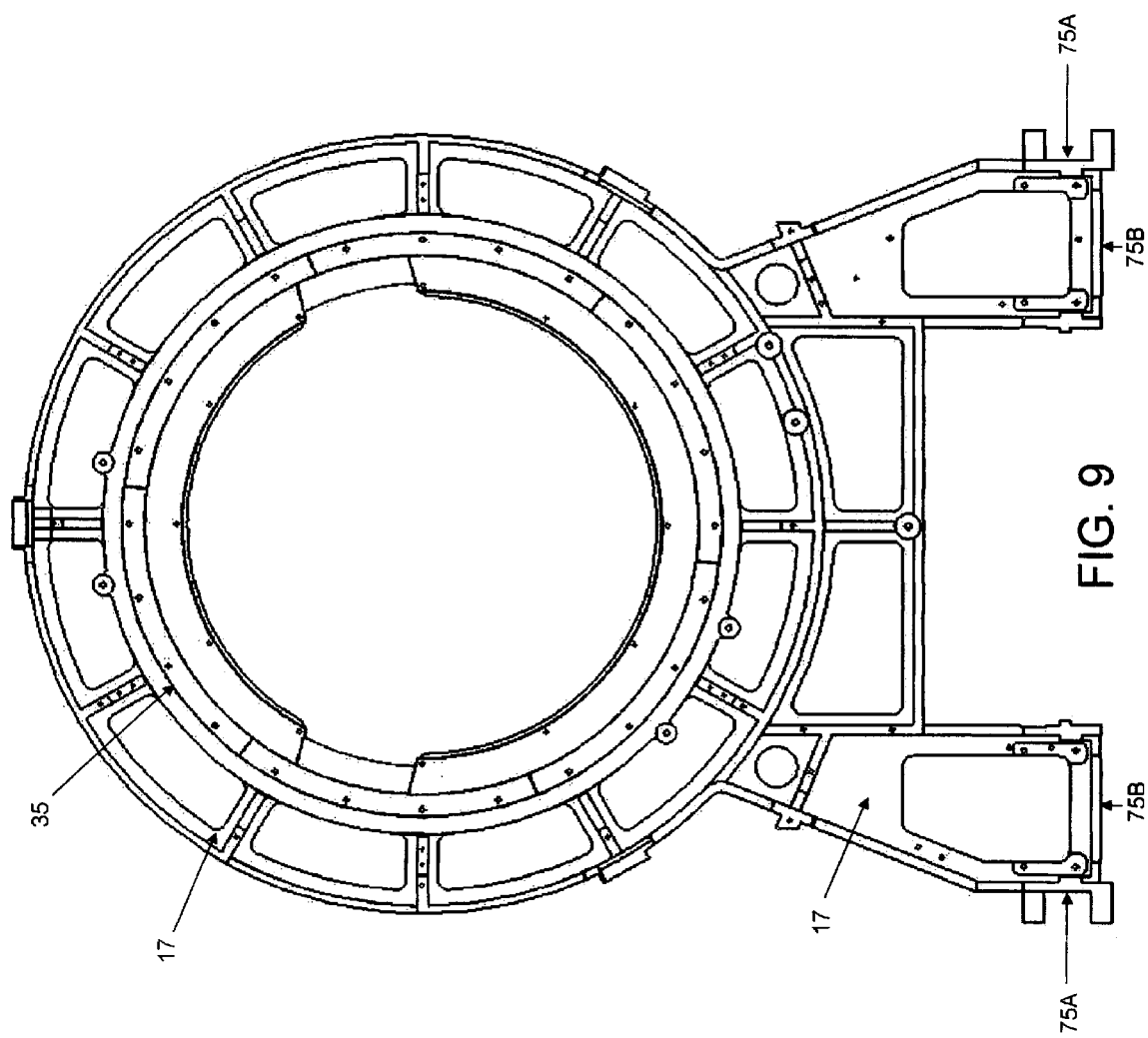
FIG. 9 is a schematic front view of the frame and rotating drum assembly the novel mobile CT imaging system shown in FIG. 7.
Figure 10:
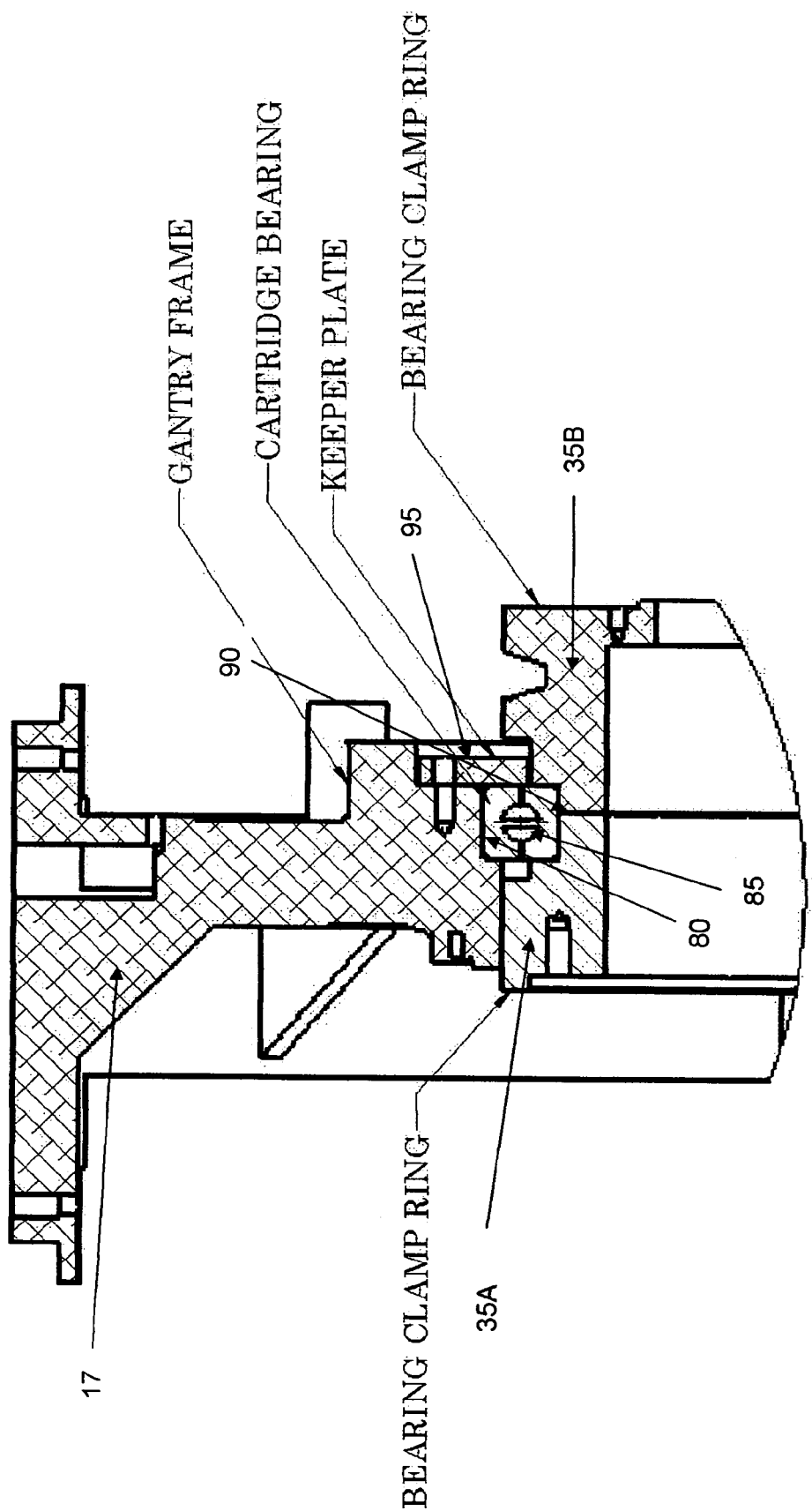
FIG. 10 is a schematic enlarged view of portions of the frame and rotating drum assembly shown in FIG. 8.

As noted above, and looking now at FIGS. 4-6, mobile CT imaging system 5 comprises a frame 17 having a uni-body construction, connecting (at its bottom end) directly to transport mechanism 50, and serving (at its top end) as one race for a bearing mechanism interposed between frame 17 and rotating drum assembly 35.

Figure 4:
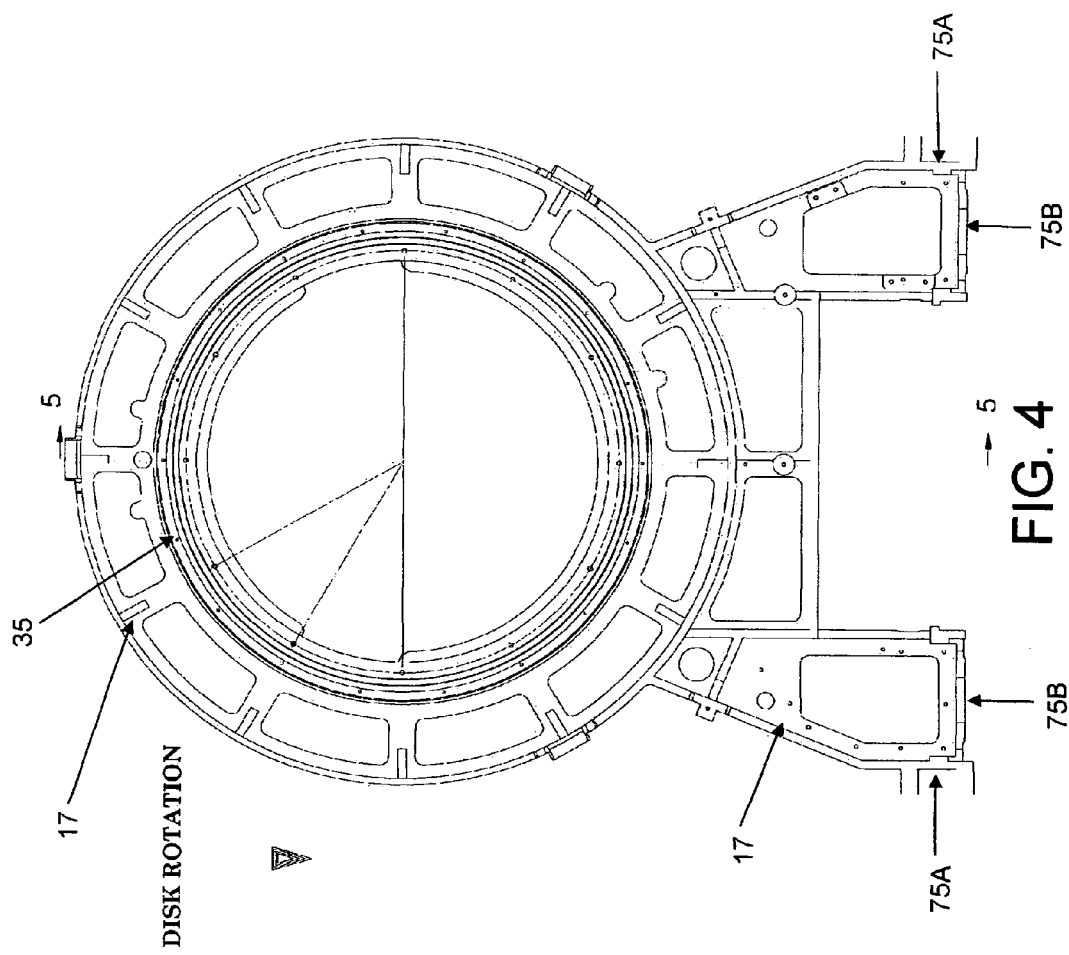
FIG. 4 is a schematic front view of the frame and rotating drum assembly of the novel mobile CT imaging system shown in FIGS. 1-3.

More particularly, at its bottom end, and looking now at FIGS. 3 and 4, frame 17 comprises one or more surfaces 75 for connecting transport mechanism 50 to frame 17. Preferably, frame 17 comprises a plurality of surfaces 75A for mounting gross movement mechanism 55 to frame 17, and a plurality of surfaces 75B for mounting fine movement mechanism 60 to frame 17.

Furthermore, at its top end, and looking now at FIGS. 3-6, frame 17 comprises a surface 80 which forms one race of a bearing 85 interposed between frame 17 and drum assembly 35. The outer surface 90 of drum 35 preferably forms the other race of bearing 85. For ease of assembly, a bearing ring 95 may be releasably mounted to frame 17 so as to facilitate positioning of bearing 85.

In an alternative form of the present invention, and looking now at FIGS. 7-10, drum assembly 35 is formed out of two halves 35A and 35B, which are secured to one another so as to capture bearing 85 therebetween, in order to facilitate positioning of bearing 85. Again, one race of the bearing 85 is formed by a surface 80 of frame 17, and the other race of the bearing is formed by surface 90 of drum 35.

The present invention provides a novel approach for forming the frame, the rotating drum assembly and the mechanical mounts, and for mounting the rotating drum assembly and its passenger components (e.g., the X-ray tube assembly and the X-ray detector assembly) to the frame, so as to facilitate the provision of a mobile CT imaging system of reduced complexity and reduced cost.

Use

The novel CT imaging system 5 is preferably used as follows. When a patient arrives at the emergency room presenting stroke-like symptoms, they are quickly scanned in the emergency room, on their gurney, using CT imaging system 5, which is pre-positioned in the emergency room. More particularly, CT imaging system 5 is raised on its gross movement mechanism 55, i.e., by actuating hydraulic actuators 65. CT imaging system 5 is then moved on its casters to the patient, so that the patient (while still lying on their gurney) is positioned within the center opening 20 of CT imaging system 5. Thereafter, hydraulic apparatus 65 is activated so that CT imaging system 5 is supported on its fine movement mechanism 60 (i.e., the centipede belt drives). Scanning is then commenced, with fine movement mechanism 60 precision-advancing CT imaging system 5 relative to the patient during scanning.

Application To Other Types Of Scanning Systems

It should be appreciated that the present invention is not limited to use in medical applications or, indeed, to use with CT machines. Thus, for example, the present invention may be used in connection with CT machines used for non-medical applications, e.g., with CT machines which are used to scan inanimate objects. Furthermore, the present invention may be used with non-CT-type scanning systems.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A CT imaging system comprising:
   a frame having a center opening, the frame being formed with a uni-body construction;
   a CT imaging unit mounted to the frame, wherein the CT imaging unit is adapted to scan anatomical objects located within the center opening and generate images of the same, wherein the CT imaging unit comprises:
      a rotatable drum assembly rotatably mounted to the frame, concentric with the center opening, wherein at least one bearing is disposed between the rotatable drum assembly and the frame, and further wherein one race of the bearing is formed by a surface of the rotatable drum assembly and the other race of the bearing is formed by a surface of the frame;
      an X-ray tube mounted on the rotatable drum assembly and configured to emit an X-ray beam; and
      an X-ray detector mounted on the rotatable drum assembly in alignment with the X-ray beam; and
   a transport mechanism mounted to the frame, wherein the transport mechanism comprises a fine movement mechanism for moving the CT imaging unit precisely, relative to the patient, during scanning;
   wherein the fine movement mechanism comprises at least one centipede belt drive unit.

2. A CT imaging system according to claim 1 wherein the fine movement mechanism is configured to move the mobile CT imaging system relative to the patient using indexed movement in discrete steps, whereby to enable slice scanning.

3. A CT imaging system according to claim 1 wherein the fine movement mechanism is configured to move the mobile CT imaging system relative to the patient using substantially continuous movement, whereby to enable helical scanning.

4. A CT imaging system according to claim 1 wherein the fine movement mechanism comprises two centipede belt drive units.

5. A CT imaging system according to claim 4 wherein one centipede belt drive unit is disposed on either side of the patient.

6. A CT imaging system according to claim 1 wherein the transport mechanism further comprises a gross movement mechanism for transporting the mobile CT imaging system relatively quickly across room distances.

7. A CT imaging system according to claim 6 wherein the gross movement mechanism comprises at least one caster unit.

8. A CT imaging system according to claim 7 wherein the gross movement mechanism comprises two caster units, each having two caster wheels.

9. A CT imaging system according to claim 8 wherein one caster unit is disposed on either side of the patient.

10. A CT imaging system according to claim 6 wherein the transport mechanism is configured so that the mobile CT imaging system is: (i) transported by the gross movement mechanism while the mobile CT imaging system is being moved across room distances to the patient; and (ii) moved precisely relative to the patient by the fine movement mechanism while the patient is being scanned by the mobile CT imaging system.

11. A CT imaging system according to claim 6 wherein the gross movement mechanism comprises an actuator for:
 (i) extending portions of the gross movement mechanism below portions of the fine movement mechanism whereby the mobile CT imaging system will be supported by portions of the gross movement mechanism; and (ii) retracting portions of the gross movement mechanism above portions of the fine movement mechanism whereby the mobile CT imaging system will be supported by portions of the fine movement mechanism.

* * * * *